US00PP35338P2

(12) United States Plant Patent
Van Swieten

(10) Patent No.: US PP35,338 P2
(45) Date of Patent: Aug. 22, 2023

(54) ***PHALAENOPSIS* ORCHID PLANT NAMED 'PHA352347'**

(50) Latin Name: ***Phalaenopsis* hybrid**
Varietal Denomination: PHA352347

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/803,968

(22) Filed: Feb. 10, 2023

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — Jondle & Associates, P.C.

(57) ABSTRACT

A new and distinct variety of *Phalaenopsis* plant named 'PHA352347', particularly characterized by having dark red flowers with small, light purple edges and red-purple lips, flowers that are flat in lateral view, recurving curvature of longitudinal axis of dorsal sepal, and medium curvature of lateral lobe of lips, and is propagated by meristem tissue culture, is disclosed.

3 Drawing Sheets

Genus and species: *Phalaenopsis* hybrid.
Variety denomination: 'PHA352347'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHA352347'.

The new *Phalaenopsis* plant is a product of a planned breeding program conducted by the inventor in Bleiswijk, the Netherlands. The objective of this breeding program was to create a new *Phalaenopsis* plant with attractive, dark red flowers with small light purple edges and red-purple lips, suitable for potted plant production.

The new *Phalaenopsis* plant 'PHA352347' is a result of cross-pollination made by the inventor in February 2014 in Bleiswijk, the Netherlands, of the proprietary female, or seed parent, *Phalaenopsis* hybrid '07-032502-0002' (unpatented) with the proprietary male, or pollen parent, *Phalaenopsis* hybrid '07-006240-0002' (unpatented).

The new *Phalaenopsis* was selected by the inventor as a single plant within the progeny of the stated cross-pollination in a controlled greenhouse in Bleiswijk, the Netherlands, in November 2016. Asexual reproduction of the new *Phalaenopsis* plant by meristem tissue culture since 2017 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Jan. 20, 2022 (Application no. 2022/0175), by Applicant who obtained the subject matter disclosed directly from the inventor. 'PHA352347' has not been made publicly available or sold anywhere in the world prior to the effective filing date of this application with the exception of sales or disclosures made one year or less before the effective filing date of this claimed invention by Applicant who obtained 'PHA352347' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHA352347' as a new and distinct variety of *Phalaenopsis* plant:

1) Dark red flowers with small light purple edges and red-purple lips
2) Flower shape in lateral view is flat;
3) Dorsal sepal: curvature of longitudinal axis is recurving; and
4) Lip: curvature of lateral lobe is medium.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in October 2022. Colors in the photographs may differ from the color values cited in the detailed botanical description, which accurately describe the actual colors of the new variety.

DESCRIPTION OF THE NEW VARIETY

Figure 1:
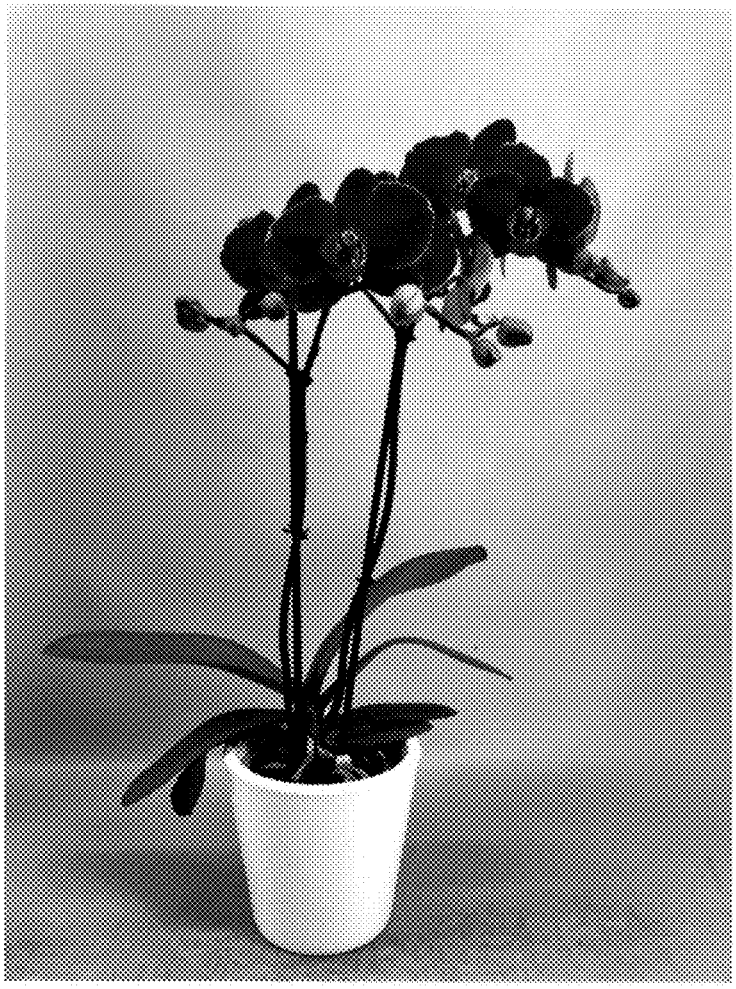
FIG. 1 shows the overall plant habit, including blooms, buds, and foliage of 'PHA352347'.
Figure 2:
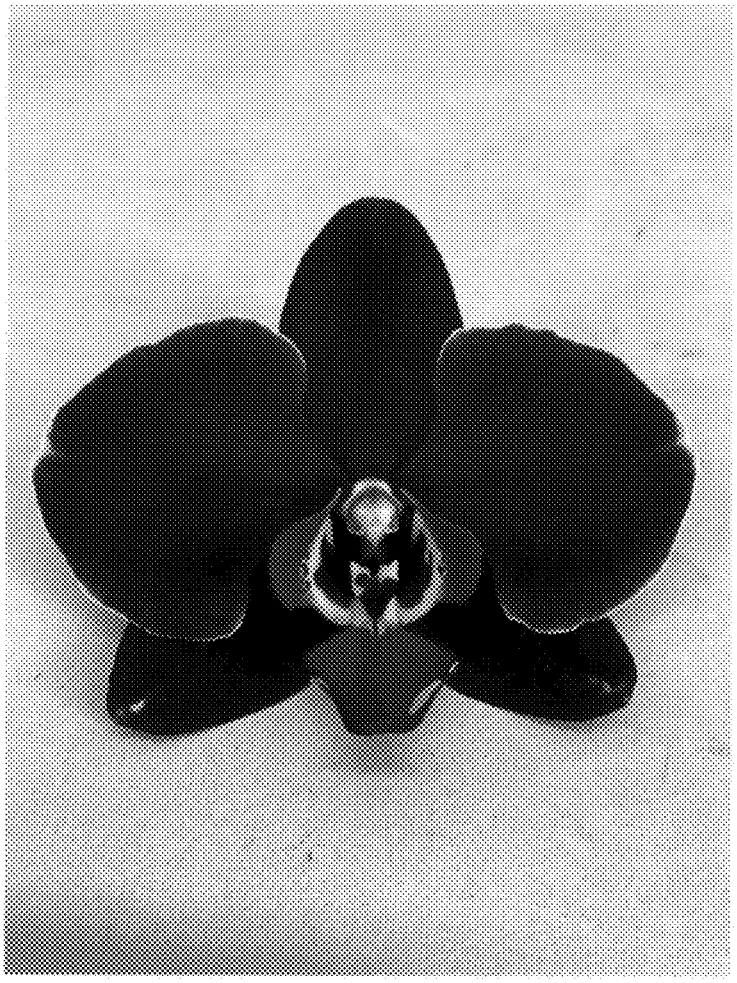
FIG. 2 shows a close-up of a flower of 'PHA352347'.
Figure 3:
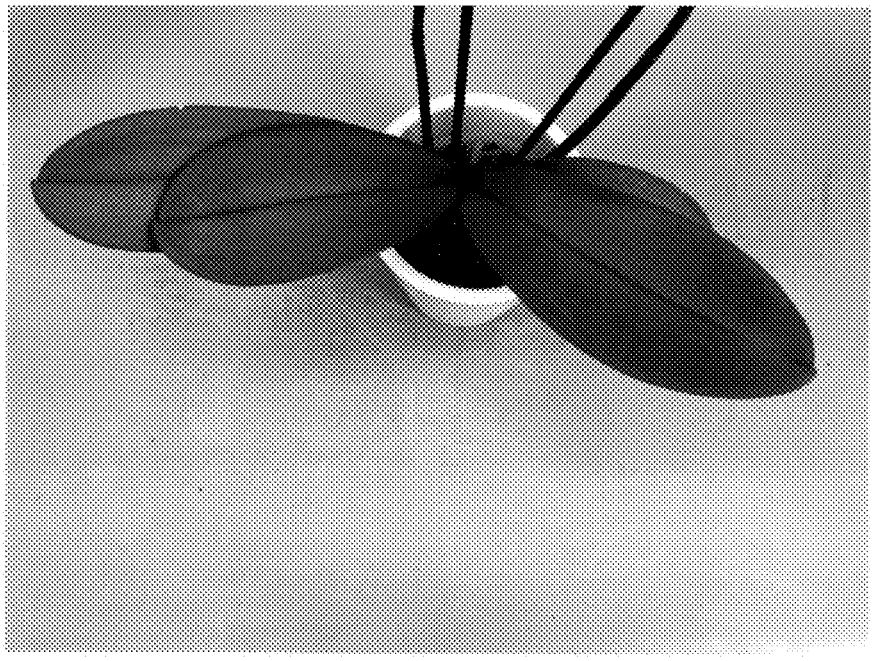
FIG. 3 shows an overhead view of the leaves of 'PHA352347'.

The following detailed description sets forth the distinctive characteristics of 'PHA352347'. Plants of the new *Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in October 2022 on flowering plants which were planted in 12-centimeter (diameter) pots. After in vitro propagation, the plants were grown in nursery trays for 20 to 24 weeks, followed by transplantation into 12-centimeter (diameter) pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:
- *Family.*—Orchidaceae.
- *Botanical.*—*Phalaenopsis* hybrid.
- *Common name.*—Moth orchid.
- *Variety name.*—'PHA352347'.

Parentage:
- *Female parent.*—*Phalaenopsis* cultivar '07-032502-0002' (unpatented).
- *Male parent.*—*Phalaenopsis* cultivar '07-006240-0002' (unpatented).

Propagation:
- *Type.*—Meristem tissue culture.

Roots:
- *Root description.*—Greyed-green (a color in between RHS 190B and RHS 190C) colored roots with branching lateral roots having yellow-green (RHS 146C) with a touch of purplish-red (RHS N77D) colored root tips.

Plant:
- *Crop time to flowering.*—Following asexual propagation (in vitro), the rooted cuttings grow for 20 to 24 weeks. After transplantation into 12-cm pots, the plant is finished after 48 to 50 weeks.
- *Growth habit of the peduncle.*—Upright to slightly pendent with panicle inflorescence.
- *Height (from soil level to top of inflorescence).*—Approximately 50.0 cm to 55.0 cm.
- *Width (measured from leaf tips).*—About 37.0 cm to 39.0 cm.
- *Vigor.*—Strong.

Leaves:
- *Mature leaves.*—Quantity per plant: 7 to 9 leaves are produced before flowering. Length (fully expanded): 21.0 cm to 23.0 cm. Width: 7.0 cm to 8.0 cm. Position of the broadest part of the leaf: Towards apex. Shape: Obovate. Base shape: Moderately elongated. Apex: Obtuse asymmetric. Leaf blade angle with the petiole (measured from the horizontal position): Between 30 degrees and 50 degrees. Leaf margin: Entire. Color: Upper surface: Green (RHS 146A). Lower surface: Yellow-green (RHS 146B) with a dark red margin and overcolor toward the tips (RHS N186C). Texture (both upper and lower surfaces): Smooth. Thickness: 2.0 mm to 3.0 mm. Variegation: Absent. Venation: Pattern: Parallel. Color of the midvein: Upper surface: Green (RHS 146A). Lower surface: Yellow-green (RHS 146B) with a touch of diluting dark red toward the tips (RHS N186C).

Peduncle:
- *Quantity per plant.*—1 to 2.
- *Number of flowers per peduncle.*—12 to 16.
- *Length.*—50.0 cm to 55.0 cm.
- *Diameter.*—5.0 mm to 6.0 mm.
- *Strength.*—Strong.
- *Aspect.*—Upright to slightly pendent.
- *Texture.*—Smooth.
- *Color.*—Mix of brown (RHS 200A) and green (RHS 146C).
- *Internode length.*—2.5 cm to 3.5 cm.

Inflorescence description:
- *Appearance.*—Upright to slightly pendent, panicle inflorescence with bilaterally symmetrical flowers that open in succession beginning with the lowermost flower.
- *Number of inflorescences.*—1 to 2.
- *Inflorescence size.*—Height (from base to tip): 210.0 mm to 260.0 mm.
- *Flowering time.*—First flowers can be expected 10 to 11 months after planting in a 12-cm pot.
- *Flower.*—Height: 85.0 mm to 90.0 mm. Diameter: 88.0 mm to 93.0 mm. Depth of lip: 20.0 mm to 22.0 mm.
- *Flower shape.*—Flat.
- *Flower longevity.*—On the plant: 11 to 14 weeks.
- *Fragrance.*—Absent.
- *Flower bud.*—Average size: Large. Length: 24.0 mm to 26.0 mm. Width: 19.0 mm to 21.0 mm. Shape: Egg shaped. Color: Yellow-green (RHS N144D) with a touch of dark purplish-red shade (RHS N79C) toward the tips.
- *Petals.*—Arrangement: Open/free. Shape: Semi-circular. Apex: Rounded, slightly asymmetric. Margin: Entire. Length (from base to tip): 39.0 mm to 41.0 mm. Width: 43.0 mm to 45.0 mm. Position of the broadest part of the petal: Toward the base. Color (when fully opened): Upper surface: Basic color: Dark red (RHS 187C). Over color: Light purple edge (a color in between RHS 76A and RHS 76B). Lower surface: Basic color: Light purple (RHS 76A). Over color: White at the base (RHS NN155C) and light reddish-purple midvein (RHS N78D). Number of spots and stripes on the petals (upper surface): None. Color of spots and stripes on the petals (upper surface): Not applicable. Density of netting of the petals (upper surface): None. Color of the netting (upper surface): Not applicable.
- *Dorsal sepal.*—Shape: Elliptic. Apex: Emarginated symmetric. Margin: Entire. Length (from base to tip): 43.0 mm to 45.0 mm. Width: 27.0 mm to 29.0 mm. Position of the broadest part of the dorsal sepals: At middle. Color (when fully opened): Upper surface: Basic color: Dark red (RHS 187C). Over color: Absent. Lower surface: Basic color: Very light purple (RHS 76B). Over color: Light yellowish-green (a color in between RHS 145C and RHS 145D) at the middle toward the tips; light purple (RHS 76A) toward margins and tips; reddish-purple midvein (RHS N78D); diluting purplish-pink stripes (RHS N78C). Number of spots and stripes on the dorsal sepals (upper surface): None. Color of spots and stripes on the dorsal sepals (upper surface): Not applicable. Density of netting of the dorsal sepals (upper surface): None. Color of the netting: Not applicable.

*Lateral sepals.*—Shape: Ovate. Apex: Obtuse asymmetric. Margin: Entire. Length (from base to tip): 43.0 mm to 45.0 mm. Width: 24.0 mm to 26.0 mm. Position of the broadest part of the lateral sepals: Toward the base. Color (when fully opened): Upper surface: Basic color: Dark red (RHS 187C). Over color: Dark red (RHS 187B) at the base; touch of light reddish-purple (RHS N78D) at the apex. Lower surface: Basic color: Very light purple (RHS 76B). Over color: Light yellow-green (a color in between RHS 145C and RHS 145D) at the base; light purple (RHS 76A) on the sides toward the tips; reddish-purple midvein (RHS NN78B) toward the tips. Number of spots and stripes on the lateral sepals (upper surface): None. Color of spots and stripes on the lateral sepals (upper surface): Not applicable. Density of netting of the lateral sepals (upper surface): None. Color of the netting (upper surface): Not applicable.

*Labellum* (*lip*).—Whiskers: Present. Length of whiskers: 10.0 mm to 12.0 mm. Color of whiskers: Reddish-purple (RHS N78A) with white (RHS NN155C), spotted tips (RHS N79B). Pubescence on the lip: Absent.

*Lateral lobe.*—Shape: Type V (as described in the International Union for the Protection of New Varieties of Plants (UPOV) Test Guidelines for *Phalaenopsis*); spatulate. Margin: Slightly undulated. Length: 19.0 mm to 21.0 mm. Width: 14.0 nun to 16.0 mm. Color: Upper surface: White (RHS NN155C) with dark red stripes (RHS 187C) at the base; a touch of greenish-yellow on one side (RHS 6B) at the base; purplish-red (RHS 61A) on the other side toward the tips; reddish-purple on the other side toward the tips (RHS N78A). Lower surface: White (RHS NN155C); a touch of greenish-yellow (RHS 6C) at the base; purplish-red (RHS 61A) and reddish-purple (RHS N78A) on one side toward the tips. Number of spots and stripes on the lateral lobe: Few stripes and few spots. Color of spots and stripes on the lateral lobe: Stripes and spots RHS 187C. Density of netting of the lateral lobe: None. Color of the netting: None.

*Apical lobe.*—Shape: Triangular. Margin: Entire. Length: 21.0 mm to 23.0 mm. Width: 19.0 mm to 21.0 mm. Color: Upper surface: Touch of yellow (RHS 8A) at the base and reddish-purple (RHS N78A) toward the whiskers. Lower surface: Purplish-pink (RHS N78C) at the middle from base toward the whiskers; red wings (RHS 184B); reddish-purple (RHS N78A) toward the whiskers. Number of spots and stripes on the apical lobe: None. Color of spots and stripes on the apical lobe: Not applicable. Density of netting of the apical lobe: None. Color of the netting: None. Bump and ride: Present; small.

*Callus.*—Average size: Medium to large. Height: 7.0 mm to 8.0 mm. Length: 5.0 mm to 6.0 mm. Width: 4.0 mm to 5.0 mm. Color: Dark red (RHS 187B) at the middle; light greenish-yellow (RHS 1D) on sides; yellow (RHS 5B) tips.

Reproductive organs:

*Column.*—Length: 9.0 mm to 10.0 mm. Diameter: 6.0 mm to 7.0 mm. Color: White (RHS NN155C) at the base; reddish-purple (RHS N78B) toward the tips.

*Pollinia.*—Quantity: 2. Diameter: 1.0 mm to 1.2 mm. Color: Orange (RHS 23A).

*Ovary.*—Length: 11.0 mm to 13.0 mm. Diameter: 2.7 mm to 3.1 mm.

*Pedicel.*—Length: 34.0 mm to 36.0 mm. Diameter: 3.2 mm to 3.7 mm. Color: Dark purplish-red (RHS N79B) spots at the base; light yellow-green (RHS 145C) and very light purple (RHS 76B) toward the flowers. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHA352347' differs from the female parent plant '07-032502-0002' (unpatented) in that 'PHA352347' has petals that are straight in the cross section and weak undulation of the margin, whereas '07-032502-0002' has petals that are convex in the cross section and moderate undulation of the margin.

'PHA352347' differs from the male parent plant '07-006240-0002' (unpatented) in that 'PHA352347' has petals that are a dark red ground color of upper side and curvature of the longitudinal axis that is recurving, whereas '07-006240-0002' has petals that are a reddish-purple ground color of upper side and curvature of the longitudinal axis that is straight.

'PHA352347' is most similar to the commercial *Phalaenopsis* plants named 'PHALHEQBOG' (unpatented) and 'PHALFOXYQ' (U.S. Plant Pat. No. 29,134). 'PHA352347' differs from the commercial variety 'PHALHEQBOG' in that 'PHA352347' has petals that are a dark red ground color of upper side with no spots on petals, whereas 'PHALHEQBOG' has petals that are very light purple ground color of upper side with many to very many spots on petals. Additionally, the leaf length of 'PHA352347' is longer than 'PHALHEQBOG'.

'PHA352347' differs from the commercial variety 'PHALFOXYQ' in that 'PHA352347' has petals that are a dark red ground color of upper side with no spots on petals, whereas 'PHALFOXYQ' has petals that are dark purplish-red ground color of upper side with medium spots on the petals. Additionally, the leaf length of 'PHA352347' is longer than 'PHALFOXYQ'.

I claim:

1. A new and distinct variety of *Phalaenopsis* plant named 'PHA352347', substantially as described and illustrated herein.

* * * * *